(12) United States Patent
Aerts (10) Patent No.: US 7,662,838 B2
(45) Date of Patent: *Feb. 16, 2010

(54) USE OF A DEOXYNOJIRIMYCIN DERIVATIVE OR A PHARMACEUTICALLY SALT THEREOF

(75) Inventor: Johannes Maria Franciscus Gerardus Aerts, Abcoude (NL)

(73) Assignee: Genzyme Corporation, Cambridge, MA (US)

(*) Notice: Subject to any disclaimer, the term of this patent is extended or adjusted under 35 U.S.C. 154(b) by 392 days.

This patent is subject to a terminal disclaimer.

(21) Appl. No.: 10/595,584

(22) PCT Filed: Oct. 29, 2004

(86) PCT No.: PCT/NL2004/000760

§ 371 (c)(1),
(2), (4) Date: May 23, 2006

(87) PCT Pub. No.: WO2005/039578

PCT Pub. Date: May 6, 2005

(65) Prior Publication Data

US 2007/0135487 A1   Jun. 14, 2007

(30) Foreign Application Priority Data

Oct. 29, 2003 (EP) .................................. 03078396
Jul. 6, 2004 (EP) .................................. 04076936

(51) Int. Cl.
*A61K 31/445* (2006.01)
*C07D 401/00* (2006.01)
*C07D 211/06* (2006.01)

(52) U.S. Cl. ............... 514/327; 514/317; 514/319; 546/192; 546/195; 540/107

(58) Field of Classification Search ............... None
See application file for complete search history.

(56) References Cited

U.S. PATENT DOCUMENTS

| 4,855,415 | A | 8/1989 | Sugiyama et al. |
|---|---|---|---|
| 6,177,447 | B1 | 1/2001 | Aerts et al. |
| 6,235,737 | B1 | 5/2001 | Styczynski et al. |
| 2003/0100504 | A1* | 5/2003 | DeAlmeida et al. ........... 514/12 |
| 2004/0204379 | A1 | 10/2004 | Cheng et al. |
| 2006/0074107 | A1 | 4/2006 | Butters et al. |
| 2006/0264467 | A1 | 11/2006 | Mugrage et al. |
| 2007/0015793 | A1 | 1/2007 | Hirth et al. |
| 2007/0066581 | A1 | 3/2007 | Aerts |

FOREIGN PATENT DOCUMENTS

WO   WO 98/02161 A   1/1998

OTHER PUBLICATIONS

Matsumoto et al. Anal Chim Acta, 1479:135-141, Mar. 2003.*
Science IP, The CAS Search Service, Freedom to Operate Search, Sep. 26, 2008, 96 pp.

* cited by examiner

*Primary Examiner*—Brian-Yong S Kwon
*Assistant Examiner*—Bong-Sook Baek
(74) *Attorney, Agent, or Firm*—Isabelle A. S. Blundell (57) ABSTRACT

The invention relates to the use of a deoxynojirimycin derivative, or pharmaceutically acceptable salt thereof, for the preparation of a medicament for the treatment of insulin resistance, hyperpigmentation and/or inflammatory processes in the skin, a fungal disease, overweight and obesity, or a microbacterial infection.

2 Claims, 7 Drawing Sheets

N-(5-adamantane-1-yl-methoxy-pentyl)deoxynojirimycin   N-hydroxyethyl-deoxynojirimycin   N-butyl-deoxynojirimycin

BIOSYNTHESIS OF MAJOR GLYCOSPHINGOLIPIDS

Ob mice: Changes in blood glucose, water intake and food intake following daily oral MZ21

MZ-21 reduces liver GM3

MZ-21 has no effect on brain gangliosides, arylsulfatide or galactosylceramide

Fig 10

N-(5-adamantane-1-yl-methoxy-pentyl)deoxynojirimycin    N-hydroxyethyl-deoxynojirimycin    N-butyl-deoxynojirimycin

US 7,662,838 B2

USE OF A DEOXYNOJIRIMYCIN DERIVATIVE OR A PHARMACEUTICALLY SALT THEREOF

FIELD OF THE INVENTION

The present invention relates to the use of a deoxynojirimycin derivative, or a pharmaceutically acceptable salt thereof, for the preparation of a medicament for the treatment of various diseases in which the synthesis of glucosylceramide and/or other glycosphingolipids play a role. Such diseases include insulin resistance, hyperpigmentation, fungal diseases and microbacterial infections. In particular the invention relates to the use of a deoxynojirimycin derivative, or a pharmaceutically acceptable salt thereof, for the preparation of medicaments for the treatment of insulin resistance. Chronic insulin resistance causes diabetes mellitus type II.

The incidence of diabetes mellitus type II is dramatically increasing. The primary underlying defect is an impaired uptake of glucose from the bloodstream by muscle and adipose tissue as the result of a reduced sensitivity to mobilize GLUT4 transporters to their cell surface in response to insulin. It is already known for many years that increased concentrations of the fatty acid palmitate are associated with aberrant glucose homeostasis. Poorly understood, however, is the molecular mechanism by which lipotoxicity causes onset and progression of diabetes. Further insight in this matter will therefore assist in improving/developing medicaments for treating insulin resistance and diabetes mellitus type II.

Molecular Mechanism of Lipopathogenesis

Research activities on glycosphingolipids and diabetes mellitus type II in the Department of Biochemistry at the Academic Medical Center/University of Amsterdam has recently led to an unexpected new insight in the lipopathogenesis of diabetes mellitus type II. The underlying mechanism is described in detail below.

Role for Glycosphingolipids in Acquired Insulin Resistance

Figure 1:
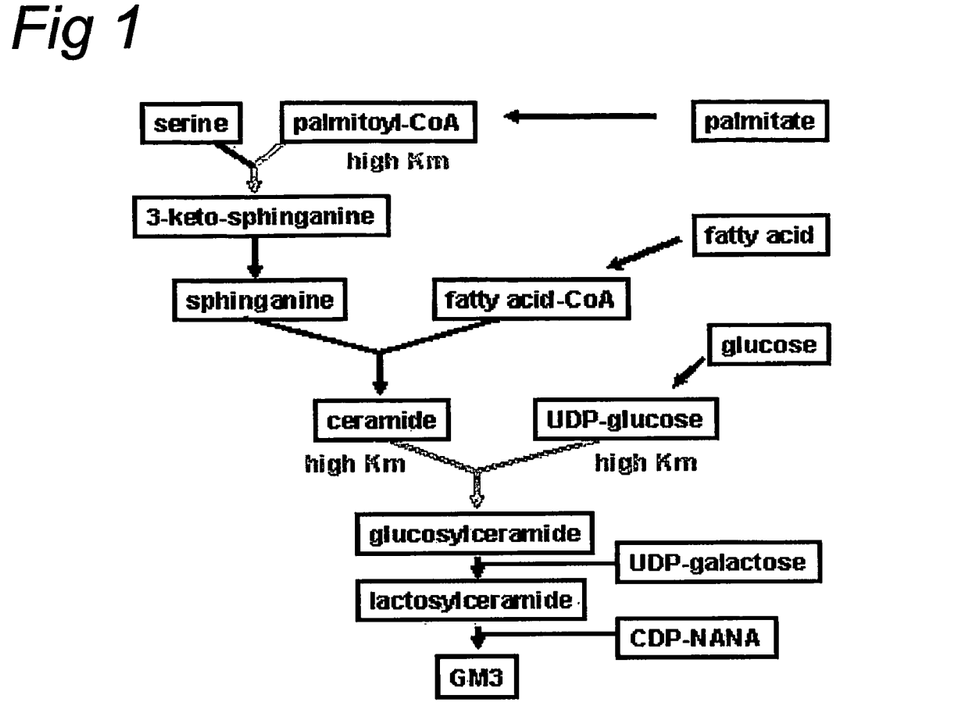
FIG. 1: Overview of GM3 formation: rate limiting are palmitate and conversion of ceramide+UDP-glucose to glucosylceramide

A role is hypothesized for (glyco)sphingolipids in the pathogenesis of insulin resistance. This thought stems from the ignored fact that palmitate is the essential building block of the ceramide moiety in sphingolipids: the first step of their biosynthesis involves the transfer of palmitate to serine, catalyzed by serine palmitoyltransferase, see FIG. 1. The rate of synthesis of sphingolipids in the liver is highly dependent on the concentration of palmitate. Importantly, this could be experimentally confirmed for cultured muscle cells (smooth muscle cells, myoblasts): addition of 0.1, 0.5, 1.0 mM palmitate in the culture medium led to proportional increases in the synthesis of glycosphingolipids, as revealed by increased incorporation of radio-labelled serine in these structures.

Figure 2:
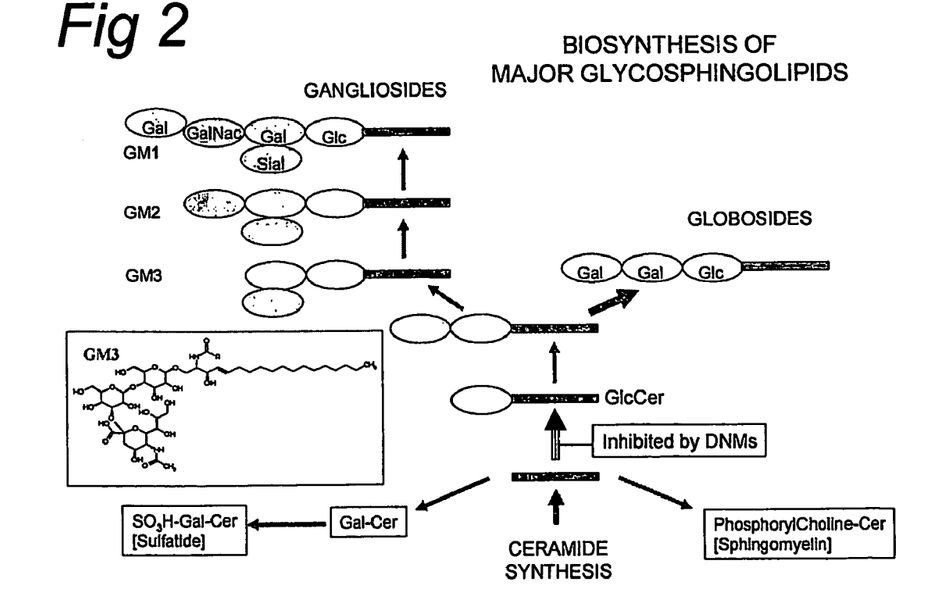
FIG. 2: Biosynthesis of major glycosphingolipids

This finding prompted a more detailed examination of the possibility that actually (glyco)sphingolipids mediate the lipotoxicity in muscles that underlies insulin resistance. It has recently been evidenced that GM3 (the most simple ganglioside at the cell surface, see FIG. 2) may impair insulin signalling. In this respect it is observed that the concentration of GM3 at the cell surface appears to regulate the uptake of glucose in response to insulin by negatively interfering with multi-clustering of insulin receptors. Moreover, high concentrations of GM3 are associated with reduced mobilization of GLUT4 to the cell surface. Conversely, reduction of GM3 is associated with enhanced insulin sensitivity (see Yamishita et al. Proc Natl Acad Sci USA (2003) 100, 3445-9 Enhanced insulin sensitivity in mice lacking ganglioside GM3; Tagami et al. (2002) J Biol Chem 277,3085-92 Ganglioside GM3 participates in the pathological conditions of insulin resistance). We postulate that at obese conditions, palmitate levels are chronically high and that therefore the formation of glycosphingolipids in adipocytes as well as muscle cells will occur at increased rates, favouring insulin resistance. The connection between increased concentration of palmitate in muscle as driving force for the increased local glycosphingolipid synthesis (including GM3) and insulin resistance (see FIG. 3) has not yet been recognised by others.

Crucial Role of Glucosylceramide Synthase

Figure 3:
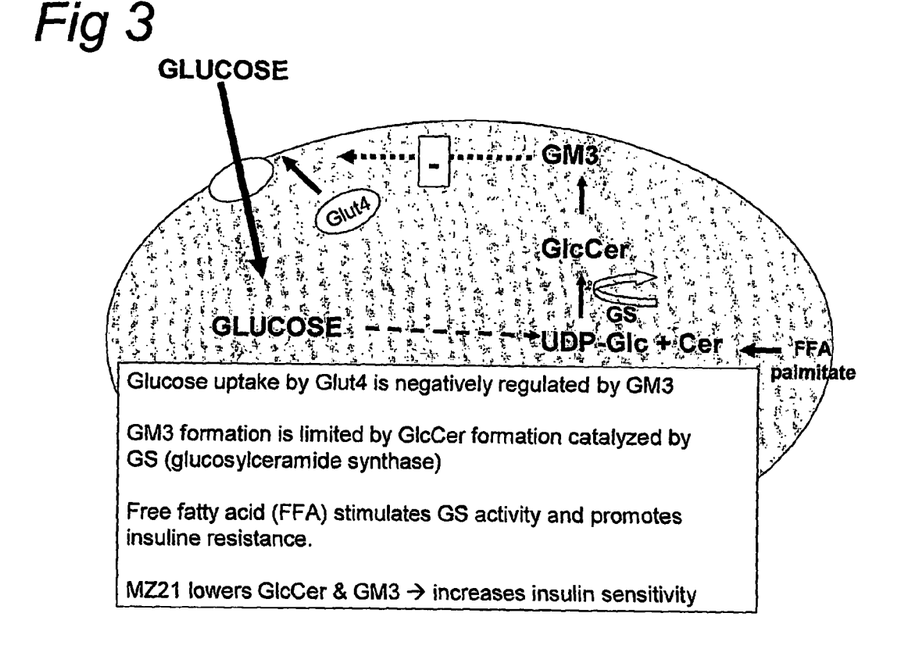
FIG. 3: Concept lipo-pathogenesis muscle in diabetes mellitus type II: key regulatory role for glucosylceramide synthase.
Figure 4:
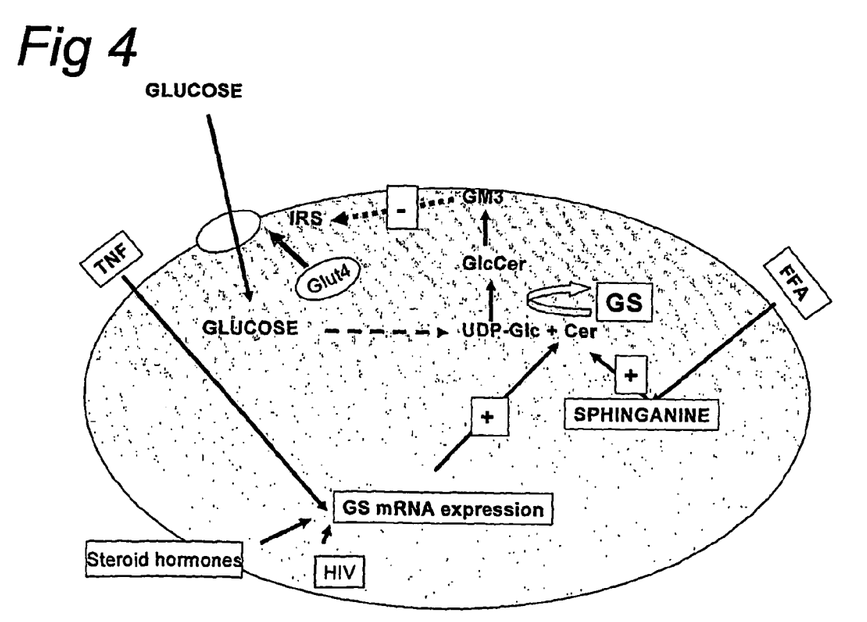
FIG. 4: Risk factors for diabetes: promoters of GlcCer formation
Figure 5:
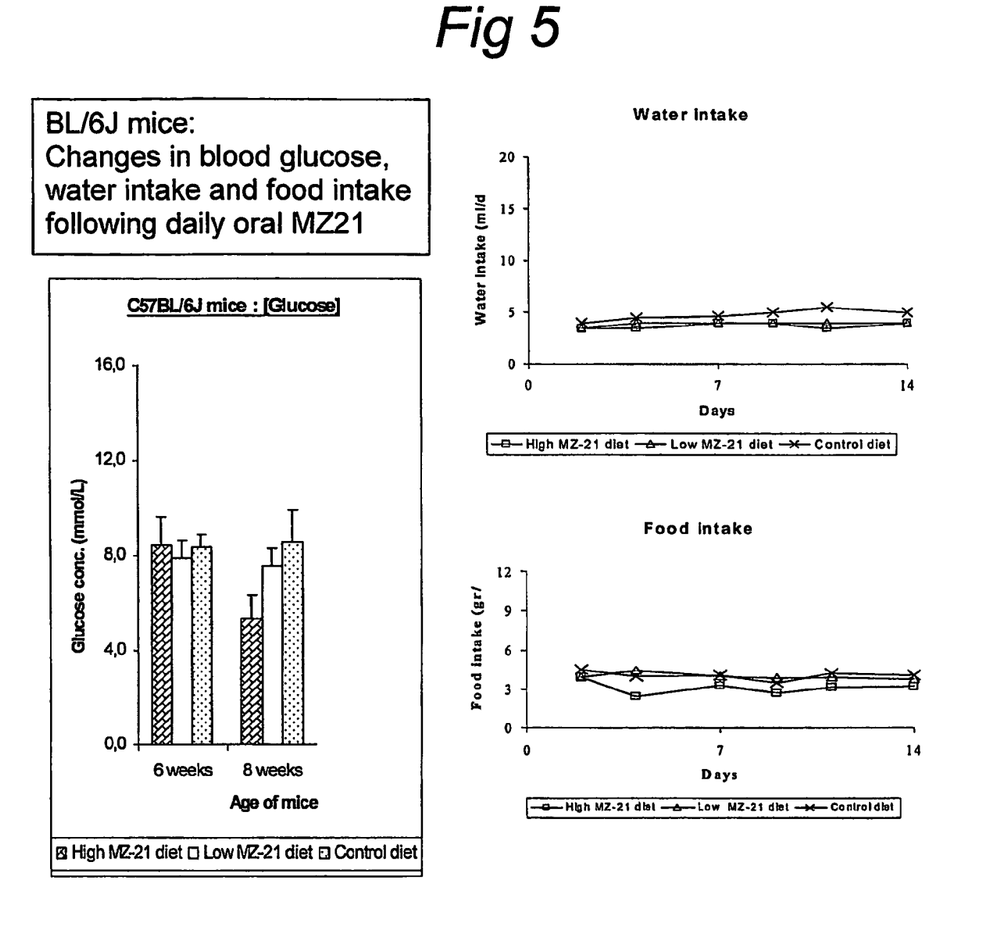
FIG. 5: Effect of daily oral administration of x mg N-(5-ADAMANTANE-1-YL-METHOXY-PENTYL)DEOXYNOJIRIMYCIN /kg) on C57B16 mice (means of 5 animals) (MZ-21=N-(5-ADAMANTANE-1-YL-METHOXY-PENTYL)DEOXYNOJIRIMYCIN)

It was further realised that the concentration of GM3 and other gangliosides at the cell surface is dependent on the activity of glucosylceramide synthase (the synthesis of glucosylceramide), the rate limiting step in ganglioside synthesis (see FIG. 3). This enzyme catalyzes the formation of glucosylceramide from ceramide and UDP-glucose. The Km values of both its substrates (ceramide and UDP-glucose) are in the physiological range. We show that glucosylceramide synthase is a key regulatory enzyme with respect to insulin sensitivity. Increases in its activity have been observed and reported previously in response to inflammatory cytokines (TNF-alfa), steroid hormones, saturated fatty acid, and viral infection (see FIG. 4). It has now surprisingly been found that the changes in glycosphingolipid synthesis have an impact on the promotion of insulin resistance which may eventually develop into diabetes mellitus type II. This finding that lipopathogenesis impacts insulin resistance shows that inhibition of glucosylceramide synthase activity exerts a beneficial, anti-hyperglycaemic effect.

SUMMARY OF THE INVENTION

Novel Use of Imunosugar-Based Inhibitors

It has become clear that deoxynojirimycins, a particular category of iminosugars, are suitable agents to reduce glycosphingolipid synthesis by the inhibition of the synthesis of glucosylceramide. Further, considerable hands-on expertise has been obtained with the safety of iminosugar administration in humans.

Accordingly, the present invention relates to the use of an inhibitor of glucosylceramide synthase, said inhibitor being a deoxynojirimycin derivative, for the preparation of a medicament for the treatment of insulin resistance.

As insulin resistance is found in most people who are diagnosed with metabolic syndrome, a further embodiment of the use according to the invention is for the treatment of metabolic syndrome.

Glucosylceramide synthase is not the only enzyme that is inhibited by deoxynojirimycins. In fact several 'glucose-processing' enzymes at the cell surface and in different intracellular compartments are inhibited by deoxynojirimycins (see Butters et al. Chem. Rev. (2000), 100: 4683-96). The consequences of administration of deoxynojirimycins in vivo do not always correlate with in vitro potency against target enzymes, due to the different accessibility of the drug to different compartments of the cell. For instance N-butyl-deoxynojirimycin is a potent glycan trimming α-glucosidase inhibitor in vitro (sub-μM $K_i$) and only a modest inhibitor of glucosylceramide synthase (glycosphingolipid synthesis is only 20-30% inhibited by 100 mg TID N-butyl-deoxynojirimycin). Nevertheless, due to the greater accessibility of the latter enzyme to the drug (the catalytic domain of glucosylceramide synthase is facing the cytosol, whereas α-glucosidases reside in the ER). N-butyl-deoxynojirimycin has been recently registered for the treatment of type 1 Gaucher disease based on its ability to inhibit glycosphingolipid biosynthesis.

Thus in vivo evaluation is essential in order to establish how significant potential inhibitory activities of deoxynojirimycins are.

A suitable inhibitor should have an IC50 value in vivo for glucosylceramide synthase of less than 1 mM, as determined by an in vivo measurement of glucosylceramide synthase activity employing cultured cells as described in the examples. Preferably the IC50 is less than 0.5 mM, more preferably less than 0.1 mM and even more preferably less than 0.05 mM.

It is preferred that the inhibitor of glucosylceramide synthase inhibits other enzymes as little as possible. In this context in particular intestinal enzymes are of relevance since potent inhibitors of intestinal glycosidases can cause severe intestinal complaints and may not be very well tolerated by many individuals. Thus it is preferred the deoxynojirimycin derivative is not a potent inhibitor of intestinal sucrase, maltase and/or lactase. Inhibition of sucrase, maltase and/or lactase that are located at the surface of enterocytes can be suitably determined in an in vitro assay employing homogenates of intestine. A deoxynojirimycin derivative is considered not to be a potent inhibitor of sucrase, maltase and/or lactase if the IC50 value in vitro is 0.5 mM or more, preferably more than 1 mM, more preferably more than 2.5 mM, more preferably more than 5 mM for at least one of sucrase, maltase and lactase, preferably for at least two of sucrase, maltase and lactase, more preferably for each of sucrase, maltase and lactase as determined by an in vitro measurement of glucosidase activity employing a membrane preparation as described in the examples.

Deoxyojirimycin derivates displaying an in vivo IC50 for glucosylceramide synthase of less than 1 mM and an in vitro IC50 value for sucrase, maltase and/or lactase, preferably for at least sucrase, of 0.5 mM or more have the desired selectivity to be used for the treatment of insulin resistance with a concomitant acceptable level of side effects in the form of intestinal complaints.

Other enzymes that are preferably inhibited as less as possible are the lysosomal glucocerebrosidase and debranching enzyme. Preferably the IC50 value for glucocerebrosidase, as established in cultured cells should exceed 0.5 mM. Preferably the IC50 value for debranching enzyme should exceed 0.5 mM.

Suitable deoxynojirimycin derivatives that can be used in accordance with the present invention are described in EP 947, EP 193770, U.S. Pat. No. 4,940,705, EP 481950, WO 95/22975, WO 00/33843, WO 01/07078 which documents are hereby incorporated by reference. For example suitable deoxynojirimycin derivatives that can be used in accordance with the present invention are N-butyl-deoxynojirimycin and N-[β-(4-ethoxycrbonylphenoxy)-ethyl]-deoxynojirimycin (emiglitate). A deoxynojirimycin derivative that is not suitable to be used in accordance with the present invention is N-hydroxyethyl-deoxynojirimycin (miglitol). Its IC50 value for glucosylceramide synthase in cultured cells exceeds 1 mM and its IC50 value for sucrase is below 5 mM.

In one embodiment deoxynojirimycin derivates that can suitably be used in accordance with the present invention are described in WO 98/02161 and J. Biol. Chem. 273, 26522-27(1998), which documents are both hereby incorporated by reference. Preferably, the deoxynojirimycin derivative comprises an apolar side chain linked to the nitrogen atom of deoxynojirimycin. Preferably, the apolar side chain comprises a large hydrophobic moiety which is derived from a polycyclic alcohol containing three or more rings each sharing two or more carbon atoms with another ring and which is capable of inserting in lipid bilayers. Preferably, the large hydrophobic moiety is linked to said nitrogen atom of the deoxynojirimycin by means of a spacer comprising an alkoxy polyalkylene or polyalkylene chain of from 3 to 8 carbon atoms. More preferably, the large hydrophobic moiety is derived from a compound selected from the group consisting of adamantanemethanol, cholesterol, β-cholestanol, adamantanol and 9-hydroxyphenanthrene. The word 'spacer' refers to any bivalent moiety or group capable of linking a hydrophobic group to the N atom of deoxynojirimycine.

Design of a Specific Inhibitor

In particular N-(5-adamantane-1-yl-methhoxy-pentyl) deoxynojirimycin; formerly also known as AMP-DNM, has been identified as a very potent inhibitor of the glucosylceramide synthase (IC50 ~100 nM in cultured cells), which is explained by the fact that molecular modelling of the enzyme structure reveals that it has a near perfect fit in the catalytic site. N-(5-adamantane-1-yl-methoxy-pentyl)deoxynojirimycin has various additional attractive features. In addition the compound shows a good oral bioavailability.

Hence, the deoxynojirimycin derivative is preferably N-(5-adamantane-1-yl-methoxy-pentyl)deoxynojirimycin or a derivative or analogue thereof.

Other Therapeutic Approaches

It has further been found that the above-mentioned deoxynojirimycin derivatives can be used for treating hyperpigmentation and/or inflammatory processes in the skin. Therefore, the present invention also relates to the use of a deoxynojirimycin derivative, or a pharmaceutically acceptable salt thereof, for the preparation of a medicament for the treatment of hyperpigmentation and/or inflammatory processes in the skin. Preferably, the present invention relates to the use of a deoxynojirimycin derivative, or a pharmaceutically acceptable salt thereof, for the preparation of a medicament for the treatment of hyperpigmentation and/or inflammatory processes in the skin, which deoxynojirimycin derivative or salt displays a capacity for the inhibition of the synthesis of glucosylceramide and/or other glycosphingolipids.

It has also been found that the above-mentioned deoxynojirimycin derivatives can suitably be used in the treatment of fungal diseases. Hence, the present invention further relates to the use of a deoxynojirimycin derivative, or pharmaceutically acceptable salt thereof, for the preparation of a medicament for the treatment of a fungal disease. Preferably, the present invention further relates to the use of a deoxynojirimycin derivative, or a pharmaceutically acceptable salt thereof, for the preparation of a medicament for the treatment of a fungal disease, which deoxynojirimycin derivative or salt displays a capacity for the inhibition of the synthesis of glucosylceramide and/or other glycosphingolipids.

Further, it has been found that the above-mentioned deoxynojirimycin derivatives can suitably be used in the treatment of microbacterial infections. The present invention relates therefore also to the use of a deoxynojirimycin derivative, or a pharmaceutically acceptable salt thereof, for the preparation of a medicament for the treatment of a microbacterial infection. Preferably, the present invention relates therefore also to the use of a deoxynojirimycin derivative, or a pharmaceutically acceptable salt thereof, for the preparation of a medicament for the treatment of a microbacterial infection, which deoxynojirimycin derivative or salt displays a capacity for the inhibition of the synthesis of glucosylceramide and/or other glycosphingolipids. It has also been found that the above-mentioned deoxynojirimycin derivatives can suitably be used in the treatment of overweight and obesity. The present invention relates therefore also to the use of a deoxynojirimycin derivative, or a pharmaceutically acceptable salt thereof, for the preparation of a medicament for the treatment of overweight and obesity. Preferably, the present invention relates therefore also to the use of a deoxynojirimycin derivative, or a pharmaceutically acceptable salt thereof, for the preparation of a medicament for the treatment of overweight and obesity, which deoxynojirimycin derivative or salt displays a capacity for the inhibition of the synthesis of glucosylceramide and/or other glycosphingolipids.

The present invention also relates to a method of treatment of an individual suffering from a disease selected from the group consisting of insulin resistance, hyperpigmentation and/or inflammatory processes in the skin, fungal diseases, overweight and obesity, and microbacterial infections, comprising administrating to said individual an effective amount of a medicament comprising a deoxynojirimycin derivative, or a pharmaceutically acceptable salt thereof, and a pharmaceutically acceptable carrier.

The selection of a suitable route of administration and suitable formulations of pharmaceutical compositions is within the normal skills of the persons skilled in the art. Examples of suitable administration routes are parental (intravenous, subcutaneous, intramuscular) injections or infusions, oral ingestion, and topical application.

EXPERIMENTAL PART

Animal studies have indicated that N-(5-adamantane-1-yl-methoxy-pentyl)deoxynojirimycin is well tolerated and does not result in any overt pathology. In view of this, it was examined whether N-(5-adamantane-1-yl-methoxy-pentyl)deoxynojirimycin is able to reduce GM3 levels at the surface of cells. For this purpose, cells were exposed for 3 days to N-(5-adamantane-1-yl-methoxy-pentyl)deoxynojirimycin, and GM3 expression was assessed by FACS analysis with a monoclonal antibody specific to the ganglioside. In various cell types (including muscle cells), surface GM3 was potently reduced. The IC50 value for surface GM3 reduction was about 250 nM. Next the ability of N-(5-adamantane-1-yl-methoxy-pentyl)deoxynojirimycin to inhibit various glycosidases and glucosyltransferases was studied and compared to that of other known and designed iminosugars. As will be clear from Table 1, N-(5-adamantane-1-yl-methoxy-pentyl)deoxynojirimycin is from all iminosugars investigated by far the most potent and specific inhibitor of the synthesis of glucosylceramide. Variations in hydrophobic moiety (adamantanemethyl, adamantanyl, phenantryl, cholesteryl and cholestanyl) and spacer (length 3-8 carbon atoms and presence of carbonyl moiety) indicated that N-(5-adamantane-1-yl-methoxy-pentyl)deoxynojirimycin is the most optimal inhibitor.

Next, the ability of N-(5-adamantane-1-yl-methoxy-pentyl)deoxynojirimycin to inhibit the synthesis of various glycosidases and glucosyltransferases was studied and was compared to that of other known and designed iminosugars.

The value of N-(5-adamantane-1-yl-methoxy-pentyl)deoxynojirimycin as suppressor of hyperglycaemia was studied in mouse models of obesitas.

C57BL/6J mice (ob–/–, db –/–, and +/+) were orally treated with 0, 25 or 100 mg N-(5-adamantane-1-yl-methoxy-pentyl)deoxynojirimycin /kg body weight daily. Plasma glucose, water intake and food intake were monitored.

Figure 6:
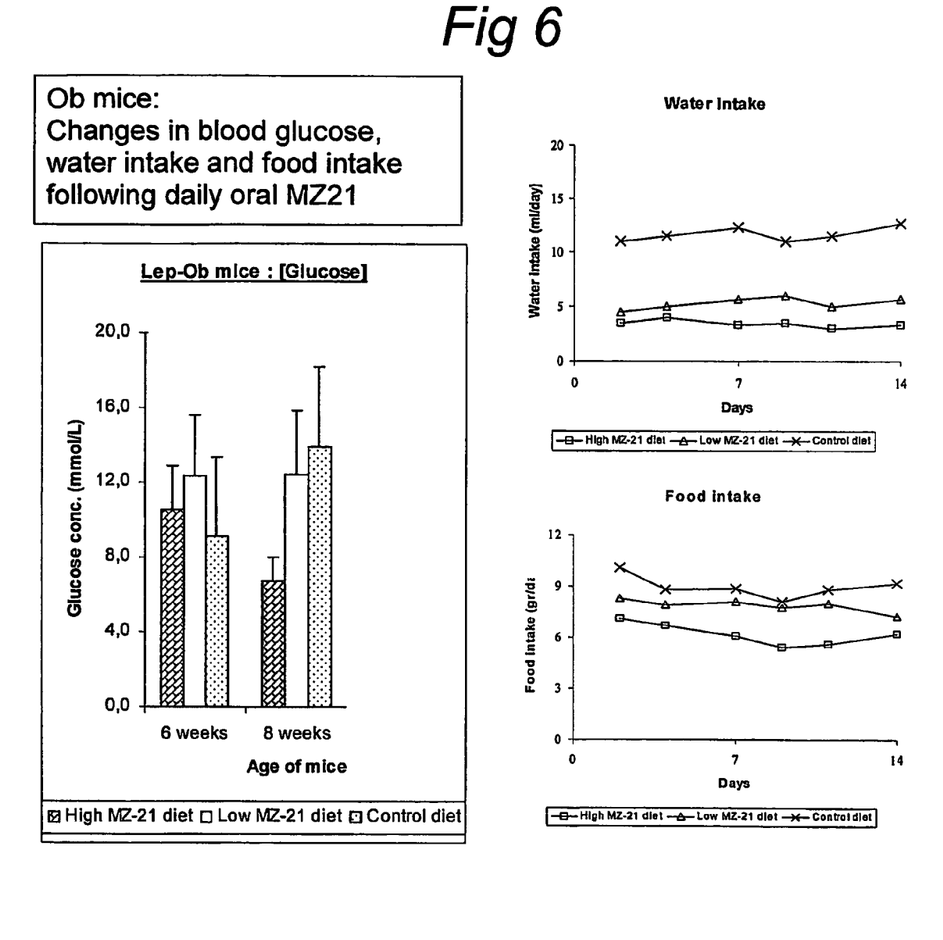
FIG. 6: Effect of daily oral administration of x mg N-(5-ADAMANTANE-1-YL-METHOXY-PENTYL)DEOXYNOJIRIMYCIN /kg) on C57B16 mice 0b–/0b–(means of 5 animals)
Figure 7:
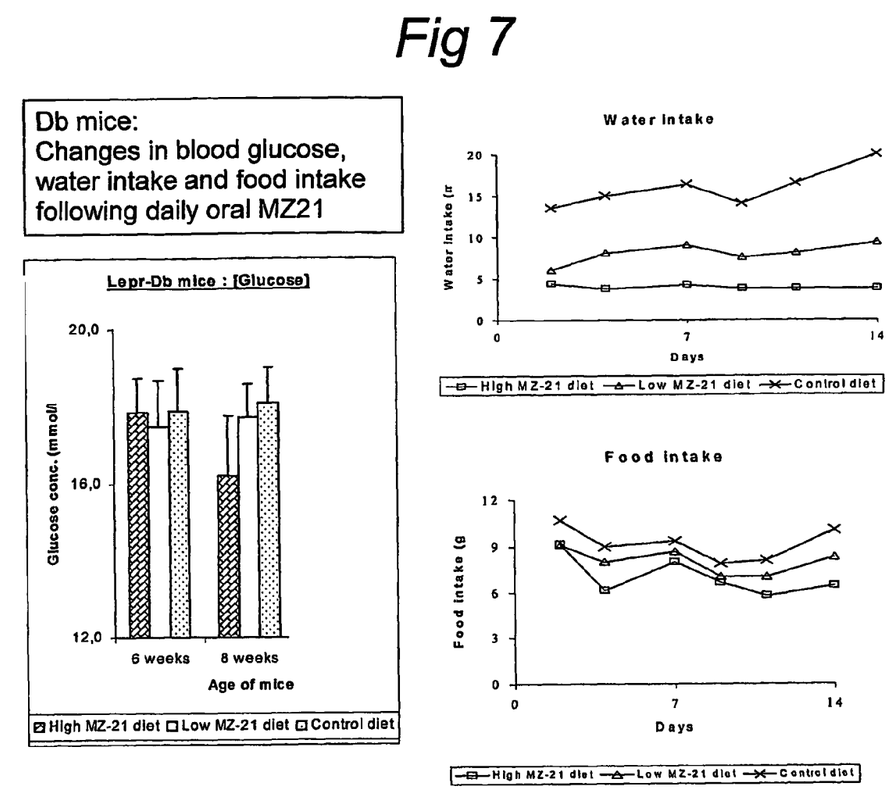
FIG. 7: Effect of daily oral administration of x mg N-(5-ADAMANTANE-1-YL-METHOXY-PENTYL)DEOXYNOJIRIMYCIN /kg) on C57B16 mice db–/db–(means of 5 animals)

The administration of N-(5-adamantane-1-yl-methoxy-pentyl)deoxynojirimycin by food resulted in the obese and diabetes mice (in dose-dependent) in reductions of blood glucose and water intake. See FIGS. 6-7. Even in normal mice a small reduction in blood glucose was already noted.

Figure 8:
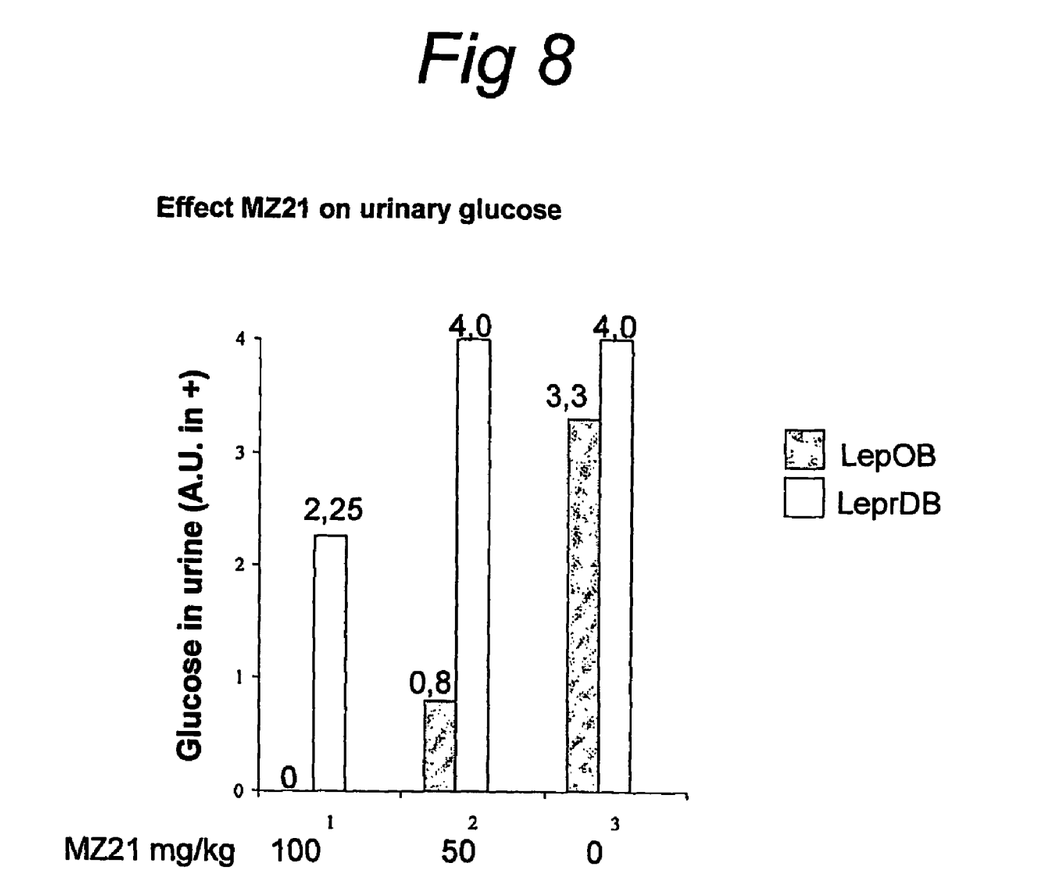
FIG. 8: Effect of daily administration of MZ21 on urinary glucose after 2 wks treatment.

Furthermore, a major reduction in urinary glucose was noted after 2 weeks treatment, particularly in ob–/ob–mice at the highest dose of N-(5-adamantane-1-yl-methoxy-pentyl) deoxynojirimycin. See FIG. 8.

Similar effects as presented in FIGS. 5-8 were noted in various independent experiments. These results are a firm proof that N-(5-adamantane-1-yl-methoxy-pentyl)deoxynojirimycin can be used as an anti-hyperglycaemic agent for the treatment of diabetes mellitus type II.

Figure 9:
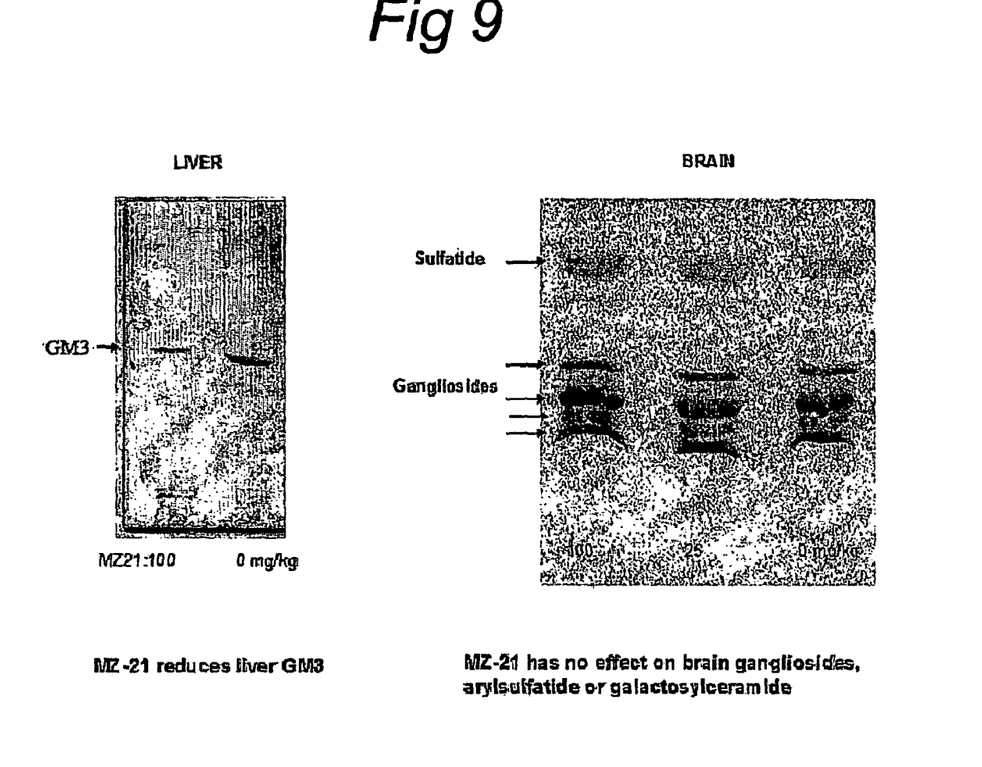
FIG. 9: Changes in gangliosides in tissues of N-(5-ADAMANTANE-1-YL-METHOXY-PENTYL)DEOXYNOJIRIMYCIN treated mice (2 wks 100 mg/kg).

In FVB and C57BL/6J mice the effect of oral administration of N-(5-adamantane-1-yl-methoxy-pentyl)deoxynojirimycin on (glyco)sphingolipids was studied to validate the mode of action of N-(5-adamantane-1-yl-methoxy-pentyl) deoxynojirimycin. Using a very sensitive and accurate HPLC-based method, ceramide and glucosylceramide levels in treated (100 mg N-(5-adamantane-1-yl-methoxy-pentyl) deoxynojirimycin /kg) and matched untreated mice were compared. Liver, muscle and brain were analyzed. No changes in ceramide concentration in any of these tissues were noted. Concomitantly the liver glucosylceramide was reduced by 80% and muscle glucosylceramide by 50%. No changes were detected in brain galactosylceramide concentration. TLC analysis was employed to monitor the effects on gangliosides. A marked reduction was noted in the liver GM3 (see FIG. 9). A reduction was also observed in muscle GM3 (not shown). No changes were noted in brain gangliosides or sulfatide (FIG. 9).

The findings on glycoshingolipids levels in the liver are consistent with the finding that plasma levels of N-(5-adamantane-1-yl-methoxy-pentyl)deoxynojirimycin are ~1 uM (4 weeks 100 mg N-(5-adamantane-1-yl-methoxy-pentyl) deoxynojirimycin /kg orally, as determined by enzymatic method). Apparently, N-(5-adamantane-1-yl-methoxy-pentyl)deoxynojirimycin poorly penetrates in the brain but is capable to reach muscle tissue.

In conclusion, the changes in glycosphingolipids exerted by the oral administration of N-(5-adamantane-1-yl-methoxy-pentyl)deoxynojirimycin correlate nicely with the anti-hyperglycaemic effect of the compound. These findings clearly show the attractiveness of the present invention.

Other aspects and advantages of the present invention will be understood upon consideration of the following illustrative experiments.

Example 1

In cultured cells the insulin signaling improvement is revealed by the increased surface expression of GLUT4 by adipocytes and increased deoxyglucose uptake by cultured adipocytes and muscle cells under influence of N-(5-adamantane-1-yl-methoxy-pentyl)deoxynojirimycin. Initial experiments already confirmed this effect.

Example 2

The increase in insulin sensitivity under the influence of N-(5-adamantane-1-yl-methoxy-pentyl)deoxynojirimycin in high fat diet fed rats and obese (leptin deficient) mice can be determined using euglycemic hyperinsulinemic clamps.

The realization of the crucial role of palmitate and glycosphingolipids in insulin resistance in muscle of diabetes type II patients rendered a rationale for the development of an anti-hyperglycaemic drug. N-(5-adamantane-1-yl-methoxy-pentyl)deoxynojirimycin shows very attractive pharmacological features (bioavailability, lack of metabolism) and its oral administration does not result in any overt pathology. Importantly, N-(5-adamantane-1-yl-methoxy-pentyl)deoxynojirimycin is able to interfere directly in the pathological cascade by lowering GM3 levels in muscle of mice. Only metabolism of glycosphingolipids is affected, not that of galactosphingolipids and sphingomyelline. The inhibition of glucosylceramide formation does also not effect ceramide concentrations. Oral administration of N-(5-adamantane-1-yl-methoxy-pentyl)deoxynojirimycin results in the desired reduction of blood and urinary glucose in obese mice that suffer from diabetes mellitus type II. Proof of concept for the use of N-(5-adamantane-1-yl-methoxy-pentyl)deoxynojirimycin as anti-hyperglycaemic agent was thus obtained.

Further Selection of Optimal Anti-Hyperglycaemic Iminosugar

Another approach to intervene in diabetes mellitus type II is based on buffering the uptake of food-derived saccharide in the gastrointestinal tract by inhibition of intestinal glycosidases. Synthetic inhibitors of sucrase (Acarbose, N-hydroxyethyl-deoxynojirimycin) are based on this concept and are registered antidiabetic drugs. N-hydroxyethyl-deoxynojirimycin is the most potent antidiabetic agent which exerts its activity through inhibition of sucrase.

The big disadvantage of potent synthetic inhibitors of intestinal glycosidases like N-hydroxyethyl-deoxynojirimycin and Acarbose is, however, that they can cause severe intestinal complaints. A potent inhibition of intestinal glycosidase results in accumulation of osmotic active sugars in the gastrointestinal lumen and favours enterobacterial growth, both contributing to spasms and diarrhoea. The potent intestinal glycosidase inhibitors N-hydroxyethyl-deoxynojirimycin and Acarbose are therefore not very well tolerated by many individuals, resulting in a poor compliance and limited application.

Figure 10:
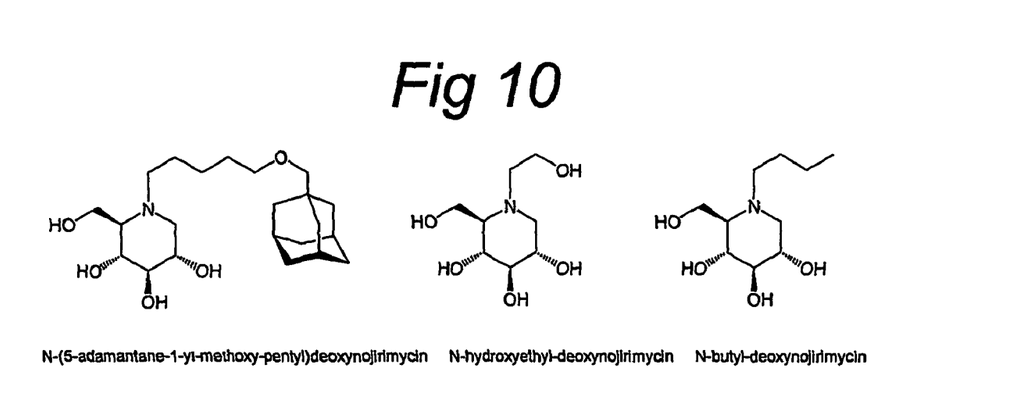
FIG. 10: Structures of cited N-substituted deoxynojirimycines.

Since a moderate inhibition of intestinal glycosidases may exert an additional beneficial effect in individuals with diabetes mellitus type II without causing the undesired intestinal complaints caused by potent inhibitors, the iminosugars were examined on this aspect. It was found that N-(5-adamantane-1-yl-methoxy-pentyl)deoxynojirimycin is also able to inhibit intestinal sucrase (IC5018 4.5 mM). The inhibition is, however, far less harsh as exerted by N-butyl-deoxynojirimycin and N-hydroxyethyl-deoxynojirimycin. Similar findings were made with respect to maltase-glycoamylase inhibition. Again N-(5-adamantane-1-yl-methoxy-pentyl)deoxynojirimycin behaved favourably when compared to N-hydroxyethyl-deoxynojirimycin and N-butyl-deoxynojirimycin. The structures of these compounds are shown in FIG. 10.

Criteria Used to Identify a Suitable Iminosugar Agent for the Treatment of Diabetes Mellitus Type II To identify the most desirable iminosugar-based agent for treatment of diabetes mellitus type II, the following set of criteria was used: the compound should be highly bioavailable when orally administered (favouring a hydrophobic character as shown by N-(5-adamantane-1-yl-methoxy-pentyl)deoxynojirimycin); the compound should be a potent inhibitor of glucosylceramide synthase; the compound should be specific and inhibit poorly the lysosomal glycosidase, alfa-glucosidase and glucocerebrosidase; the compound should not be an aggressive inhibitor of intestinal sucrase; and the compound should be metabolically inert. Fulfilment of these criteria results in a safe, effective and well tolerated anti-hyperglycaemic agent.

The deoxynojirimycin derivates used in accordance with the present invention meet these criteria. Especially, N-(5-adamantane-1-yl-methoxy-pentyl)deoxynojirimycin and structurally closely related compounds were found to be optimal agents. They are more attractive than N-butyl-deoxynojirimycin and N-hydroxyethyl-deoxynojirimycin in virtually every aspect.

Production of N-(5-adamantane-1-yl-methoxy-pentyl)deoxynojirimycin and Other Iminosugars All N-substituted iminosugars were synthesized according to the general procedure described in J. Biol. Chem, 273, 26522-27 (1998).

Enzyme Activity Assays

In vivo measurement of glucosylceramide synthase activity employing cultured cells.

Cells (melanoma cells, fibroblasts or macrophages) are cultured in a $CO_2$ incubator in 25 $cm^2$ flasks containing 3 ml medium RPMI with 50 mM HEPES. Added is 5 nmol C6-NBD-Ceramide for 1 hour. Next cells are washed and harvested by trypsinization. Lipids are extracted and analyzed following HPTLC exactly as earlier described (van Weely S, Brandsma M, Strijland A, Tager J M, Aerts J M. *Demonstration of the existence of a second, non-lysosomal glucocerebrosidase that is not deficient in Gaucher disease.* Biochim Biophys Acta. 1993 Mar. 24;1181(1):55-62). The conversion of C6-NBD-Ceramide to C6-NBD-Glucosylceramide is a direct measure for glucosylceramide synthase activity. Similarly in vivo glucocerebrosidase activity was measured as described in J. Biol. Chem, 273, 26522-27 (1998).

$IC_{50}$ values of inhibitors are determined by performing the described assay with cells incubated with variable amounts of the tested compound.

In Vitro Measurement of Activity of Glucosidases Employing a Membrane Preparation Sucrase, lactase and maltase activities were determined using freshly isolated rat intestinal membranes. Membrane homogenates were prepared by extensive washing and homogenization using a Potter and ultrasound sonication. Membrane homogenates were incubated at 0.5 M potassium phosphate (pH 6.5) for 120 min at 37° C. with either 25 mM sucrose, 25 mM lactose or 25 mM maltose. The reactions were stopped by exposure the sample for 2 minutes to 100° C. Following centrifugation the glucose content of the supernatant was determined spectrophotometrically at 550 nM using the GOD-PAP procedure (Merck) according to the manufacturer's instructions.

Debranching Enzyme

Activity measurement of debranching enzyme is based on determination of release of glucose from limit dextrin. As enzyme source erythrocytes are used since they contain no other enzymes that can degrade glycogen or limit dextrin. The substrate solution is 0.9% limit dextrin in substrate buffer (0.15 M His/NaOH (pH 6.5)+1 mM EDTA). The assay mixture is as follows. Erythrocyte homogenate (20 ul), substrate solution (40 ul). Incubation for 24 hours at 37 C. Reaction stopped by 2 minutes boiling. Centrifugation for 10.min at 10.000 rpm. The glucose content of an aliquot of the supernatant is determined with a commercial kit (Sigma).

Determination of IC50 Values

IC50 values were determined by exposing enzyme preparations to various dilutions of iminosugars and determining the concentration at which enzyme activity was reduced by 50%.

Lipid Analyses

Lipids were extracted from tissue and plasma following the well-known Bligh & Dyer procedure.

The lower (chloroform) phase was dried under nitrogen vapour. The total lipid residue was deacylated in 0.5 ml 0.1 M NaOH in methanol in a SAM-155 microwave oven for 20 minutes at 75% of maximal energy. Subsequently lipids were extracted according to the Folch procedure, and the chloroform phase was dried and lipids were resuspended in 250 ul methanol. Deacylated glycolipids were derivatised with O-phtalate and subjected to high performance liquid chromatography. HPLC analysis was conducted using a Hypersil BDS C18 column with a solvent system of methanol: 0.1 M boric acid pH 3.8 (87.5:12.5, v/v).

The upper phase of the Bligh & Dyer extraction was used for the detection of gangliosides. For this purpose, the upper phase was dried and the residue was taken up in 1 ml 0.1M NaCl, pH 4.0. The solution was passed through a C18 Sep-Pak cartridge, washed with water and the gangliosides were quantitatively eluted with chloroform:methanol (1:1). Individual gangliosides were separated on HPTLC Silica plates using chloroform:methanol:water (55:45:10 v/v/v) containing 0.2% calcium chloride. Gangliosides were subsequently visualised by spraying with the orcinol stain and quantified by densitometry.

Cell Culture

Cells (transformed smooth muscle cells, myoblasts, fibroblasts and freshly isolated rat hepatocytes) were cultured in RPMI medium in the presence of 10% foetal calf serum.

Animals

Mice (obese-lep$^{ob}$ (C57B1/6)laHsd-Lep$^{ob}$); diabetes-lepr$^{db}$ (C57B1/6KsOlaHsd—Lepr$^{db}$); wildtype (C57B1/6J OlaHsd) and wild type FVB (FVB/NHanHsd) were obtained from Harlan Nederland. Animals were fed with AM-II diet with or without N-(5-adamantane-1-yl-methoxy-pentyl) deoxynojirimycin (Hope Farms Netherlands). Mice were kept in groups of five in each cage. Water consumption and food intake were determined three times weekly per cage. Body weight of individual animals was determined three times weekly. Glucose in plasma was determined with the GOD-PAP method (Merck), and glucose in urine was determined using GLUKETUR test strips (Roche).

TABLE 1

| | IC50 value (μM) for inhibition of: | | | | | |
|---|---|---|---|---|---|---|
| Iminosugar | GCsynthase in vivo# | GlcCer-ase in vivo* | Debranching enzyme | Sucrase | Maltase | Lactase |
| N-butyl-deoxynojirimycin | 35 | 2000 | >500 | 500 | >25000 | 9000 |
| AMP-DNM | 0.3 | 1200 | >500 | 4500 | >25000 | 18000 |
| N-hydroxyethyl-deoxynojirimycin | Not inhibitory at 1 mM | Nd | Nd | 100 | Nd | Nd |

GC synthase was determined in intact cells that were fed with C6-NBD-Cer and for which formation of C6-NBD-GlcCer was monitored.
*GlcCer-ase was determined in intact cells that were fed with C6-NBD-Glcer and for which formation of C6-NBD0Cer was monitored.
AMP-DNM: N-(5-adamantane-1-yl-methoxy-pentyl)deoxynojirimycin
nd: not determined IC50 values (i.e. inhibitor concentrations resulting in 50% inhibition) were determined by variation of inhibitor concentrations. Note: N-(5-adamantane-1-yl-methoxy-pentyl)deoxynojirimycin penetrates poorly lysosomes in intact cells and IC50 values for inhibition of lysosomal glycosidase (glucocerebrosidase, acid alfa-glucosidase) are at least 20-fold higher than in vitro values.

The invention claimed is:

1. A method of treatment of an individual suffering from insulin resistance, comprising administering to said individual an effective amount of a composition comprising N-(5-adamantane-1-yl-methoxy-pentyl)deoxynojirimycin, or a pharmaceutically acceptable salt thereof and a pharmaceutically acceptable carrier.

2. A method of treatment of an individual suffering from overweight or obesity, said method comprising administering to said individual an effective amount of a composition comprising N-(5-adamantane-1-yl-methoxy-pentyl)deoxynojirimycin, or a pharmaceutically acceptable salt thereof and a pharmaceutically acceptable carrier.

* * * * *